US007887751B2

(12) United States Patent
Mimura et al.

(10) Patent No.: US 7,887,751 B2
(45) Date of Patent: Feb. 15, 2011

(54) REAGENT CASSETTE AND AUTOMATIC ANALYZER USING THE SAME

(75) Inventors: Tomonori Mimura, Tomobe (JP); Masaaki Hanawa, Hitachinaka (JP); Masaharu Nishida, Hitachinaka (JP); Yoshiaki Igarashi, Mito (JP); Yoshimitsu Takagi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 994 days.

(21) Appl. No.: 10/963,557

(22) Filed: Oct. 14, 2004

(65) Prior Publication Data

US 2005/0084426 A1      Apr. 21, 2005

(30) Foreign Application Priority Data

Oct. 17, 2003   (JP)   ............................. 2003-357163

(51) Int. Cl.
*G01N 35/00*   (2006.01)
*G01N 21/00*   (2006.01)

(52) U.S. Cl. ........................ 422/64; 422/68.1; 422/102; 436/43; 436/47; 700/266; 700/283

(58) Field of Classification Search ................ 422/68.1, 422/102, 67, 99, 100, 104, 62–65; 436/47, 436/43; 700/266, 283
See application file for complete search history.

(56) References Cited

U.S. PATENT DOCUMENTS 5,051,238 A    9/1991   Umetsu et al.
5,246,665 A    9/1993   Tyranski et al.
5,902,549 A *  5/1999   Mimura et al. ................ 422/65
6,149,872 A *  11/2000  Mack et al. .................. 422/102
7,169,356 B2 * 1/2007   Gebrian et al. ................ 422/64
2003/0044323 A1 * 3/2003 Diamond et al. ............ 422/102

FOREIGN PATENT DOCUMENTS

| AP | 5-288756   | 11/1993 |
| EP | 0290018    | 5/1988  |
| EP | 0325101    | 1/1989  |
| EP | 0445616    | 2/1991  |
| JP | 5-297007   | 11/1993 |
| JP | 5-302924   | 11/1993 |
| JP | 05-302924  | 11/1993 |
| JP | 8-058792   | 3/1996  |
| JP | 2003-066049| 3/2003  |
| WO | 03/020427  | 3/2003  |

* cited by examiner

*Primary Examiner*—Jill Warden
*Assistant Examiner*—Cedric Chan
(74) *Attorney, Agent, or Firm*—Mattingly & Malur, P.C.

(57) ABSTRACT

A reagent cassette used in an automatic analyzer for a clinical examination room, which provides an analysis environment enabling an operator to select reagent bottles with proper capacities depending on the number of tests to be performed in each different type of facility and to properly set reagents with ease. In the automatic analyzer comprising a sample pipetting section, a reagent pipetting section, a reaction cuvette, etc., one component in a sample is analyzed by using the reagent cassette in which one or a plurality of reagent bottles containing two or more types of reagents are combined together. The reagent cassette is provided with a reagent identifier including information regarding the presence or absence of a reagent opening of the reagent bottle for each of a plurality of positions of the openings.

6 Claims, 7 Drawing Sheets

FIG. 3

| REAGENT CASSETTE INFORMATION | | CONTENTS OF INFORMATION |
|---|---|---|
| REAGENT CASSETTE CODE | | 1 – 99999 |
| REAGENT SUCTION POSITION A | PRESENCE/ABSENCE OF REAGENT BOTTLE | 0:BOTTLE ABSENCE   1:BOTTLE PRESENCE |
| | SIZE OF REAGENT BOTTLE | 0:NONE    1:35ml<br>2:70ml    3:120ml |
| | REAGENT TYPE | 0:NONE              1:FIRST REAGENT<br>2:SECOND REAGENT    3:THIRD REATENT |
| REAGENT SUCTION POSITION B | PRESENCE/ABSENCE OF REAGENT BOTTLE | 0:BOTTLE ABSENCE   1:BOTTLE PRESENCE |
| | SIZE OF REAGENT BOTTLE | 0:NONE    1:35ml<br>2:70ml    3:120ml |
| | REAGENT TYPE | 0:NONE              1:FIRST REAGENT<br>2:SECOND REAGENT    3:THIRD REATENT |
| REAGENT SUCTION POSITION C | PRESENCE/ABSENCE OF REAGENT BOTTLE | 0:BOTTLE ABSENCE   1:BOTTLE PRESENCE |
| | SIZE OF REAGENT BOTTLE | 0:NONE    1:35ml<br>2:70ml    3:120ml |
| | REAGENT TYPE | 0:NONE              1:FIRST REAGENT<br>2:SECOND REAGENT    3:THIRD REATENT |
| NUMBER OF ANALYZABLE TESTS | | 1 – 9999 |

FIG.4

| REAGENT CASSETTE INFORMATION | | CONTENTS OF INFORMATION |
|---|---|---|
| REAGENT CASSETTE CODE | | 1 2 3 4 5 |
| REAGENT SUCTION POSITION A | PRESENCE/ABSENCE OF REAGENT BOTTLE | 1 |
| | SIZE OF REAGENT BOTTLE | 3 |
| | REAGENT TYPE | 1 |
| REAGENT SUCTION POSITION B | PRESENCE/ABSENCE OF REAGENT BOTTLE | 0 |
| | SIZE OF REAGENT BOTTLE | 0 |
| | REAGENT TYPE | 0 |
| REAGENT SUCTION POSITION C | PRESENCE/ABSENCE OF REAGENT BOTTLE | 0 |
| | SIZE OF REAGENT BOTTLE | 0 |
| | REAGENT TYPE | 0 |
| NUMBER OF ANALYZABLE TESTS | | 500 |

FIG.5

| REAGENT CASSETTE INFORMATION | | CONTENTS OF INFORMATION |
|---|---|---|
| REAGENT CASSETTE CODE | | 1 2 3 4 5 |
| REAGENT SUCTION POSITION A | PRESENCE/ABSENCE OF REAGENT BOTTLE | 1 |
| | SIZE OF REAGENT BOTTLE | 1 |
| | REAGENT TYPE | 1 |
| REAGENT SUCTION POSITION B | PRESENCE/ABSENCE OF REAGENT BOTTLE | 0 |
| | SIZE OF REAGENT BOTTLE | 0 |
| | REAGENT TYPE | 0 |
| REAGENT SUCTION POSITION C | PRESENCE/ABSENCE OF REAGENT BOTTLE | 0 |
| | SIZE OF REAGENT BOTTLE | 0 |
| | REAGENT TYPE | 0 |
| NUMBER OF ANALYZABLE TESTS | | 120 |

FIG.6

| REAGENT CASSETTE INFORMATION | | CONTENTS OF INFORMATION |
|---|---|---|
| REAGENT CASSETTE CODE | | 1 2 3 4 6 |
| REAGENT SUCTION POSITION A | PRESENCE/ABSENCE OF REAGENT BOTTLE | 1 |
| | SIZE OF REAGENT BOTTLE | 1 |
| | REAGENT TYPE | 1 |
| REAGENT SUCTION POSITION B | PRESENCE/ABSENCE OF REAGENT BOTTLE | 1 |
| | SIZE OF REAGENT BOTTLE | 2 |
| | REAGENT TYPE | 2 |
| REAGENT SUCTION POSITION C | PRESENCE/ABSENCE OF REAGENT BOTTLE | 0 |
| | SIZE OF REAGENT BOTTLE | 0 |
| | REAGENT TYPE | 0 |
| NUMBER OF ANALYZABLE TESTS | | 120 |

FIG.7

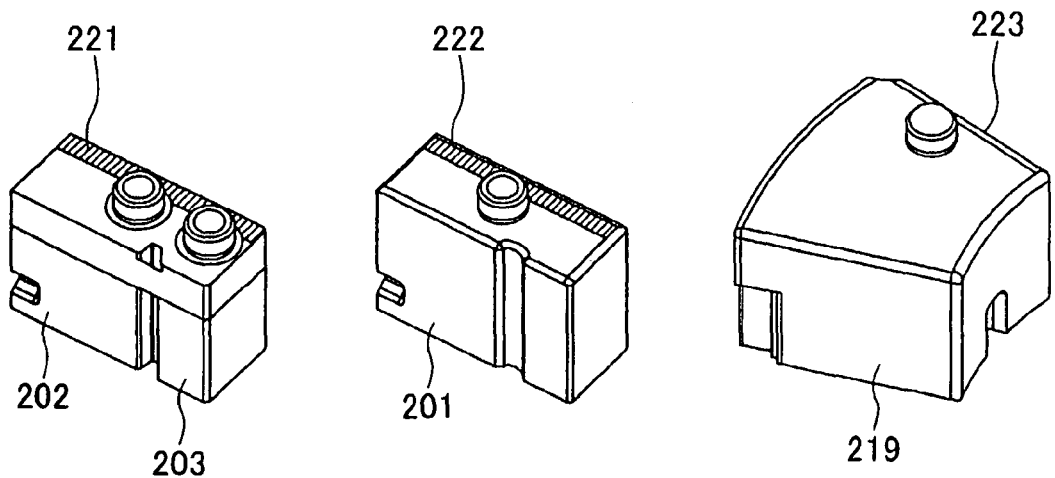

REAGENT CASSETTE AND AUTOMATIC ANALYZER USING THE SAME

BACKGROUND OF THE INVENTION

1. Field of the Invention

The present invention relates to a reagent cassette used in an automatic analyzer for carrying out qualitative and quantitative analyses of a component to be measured in a biological sample. More particularly, the present invention relates to a reagent cassette of a structure in which plural types of reagent bottles are combined together into one reagent cassette.

2. Description of the Related Art

A biochemical test for analyzing a component contained in blood of a patent is generally performed through the steps of reacting a serum obtained by centrifugal separation of the blood with a reagent, and quantitatively measuring a color developed with the reaction by a photometer. In such a test, two or more types of reagents are usually employed because it is difficult to analyze the target component by using one type of reagent from the principle point of the measurement.

The number of tests and the amounts of reagents carried out and used per day greatly differ even for the same measurement item in accordance with operating situations of various facilities depending on hospital scales such as a large general hospital and a small clinic, and measurement types such as dedicated for nighttime treatment, emergent patients and daytime patients.

Reagents have such a limitation in practical use that, because a reagent for a clinical test employs biological materials, e.g., an enzyme and an antiserum, the effective period of the reagent after opening of a reagent bottle is short. The effective period is usually about one month. Even with the same item measured in tests, if the reagent bottle has a large capacity, the reagent cannot be completely used in the effective period after opening of the reagent bottle. In other words, the reagent is discarded in some cases.

Taking into account the above-described operating situations and limitation on reagents, the reagent used even for the same measurement item is marketed as two types of commodities, i.e., a large-capacity package for use in large-scale test centers and a small-capacity bottle for use in nighttime urgent tests.

Practically, reagents have hitherto been used in two kinds of methods. According to one method shown in FIG. 9, information regarding the content of a reagent bottle is specified for each reagent bottle. According to the other method shown in FIG. 10, a plurality of reagents used for one measurement item are combined together into one reagent cassette and are employed in tests for that measurement item. Then, information regarding all the reagents is specified on the cassette.

When information regarding the content of a reagent bottle is specified for each reagent bottle according to the one method, items of information, such as the reagent type (e.g., a first reagent or a second reagent), the reagent bottle code, and the number of times of feasible measurements, are incorporated in a reagent barcode. Also, analysis parameters set in an analyzer include basic analysis conditions, such as the measurement wavelength, the sample amount and the calibration method, per measurement item and the reagent bottle code per reagent type.

When, according to the other method, a plurality of reagents used for one measurement item are combined together into one reagent cassette and employed in tests for that measurement item, and information regarding all the reagents is specified on the cassette, plural types of reagent bottles used in the test for that measurement item are put on the cassette. A combination of the reagent bottles is decided beforehand and cannot be changed. In practical use, analysis parameters for each reagent cassette are given as analysis conditions set in an analyzer and selected based on a reagent cassette code serving as a key.

The structure of one reagent cassette on which a plurality of reagent bottles are put together is disclosed in, e.g., Patent Reference 1; JP,A 5-302924.

SUMMARY OF THE INVENTION

From the above-described operating situations and limitation on reagents in clinical tests, there are problems given below. When information regarding the content of a reagent bottle is specified for each reagent bottle, an operator is required to prepare two types of reagents for each measurement item. In the case of, e.g., daytime treatment in which an operator dedicated for handling the reagents is attended, no problems occur. In the case that tests are performed, for example, in the nighttime and a not so skilled operator alternately carrying on night duty handles the reagents, however, there occurs a difficulty in management and preparations of the reagents. It is hence important that a combination of required reagent bottles, etc. could be easily selected regardless of levels of knowledge of individual operators.

Patent Reference 1 discloses that a plurality of reagent bottles used for one measurement item are arranged on one support, but it does not disclose that a recording medium attached to the support includes information regarding the capacity of each of the arranged reagent bottles (bottle size) and the presence of a reagent bottle opening (whether an opening (suction) position of the reagent bottle is located in a reagent suction position recognized by a reagent pipetting probe).

It is an object of the present invention to provide a reagent cassette which enables an analyzer to automatically recognize information regarding the size of each reagent bottle and the presence of an opening, and enables an operator to select reagent bottles with proper capacities depending on the number of tests to be performed in each different type of facility and to properly set reagents with ease even when a plurality of reagents used for one measurement item are combined together into one reagent cassette and are employed in tests for that measurement item. Another object of the present invention is to provide an automatic analyzer using the reagent cassette.

To achieve the above objects, the present invention is constructed as follows:

Two or more types of reagent bottles are combined together into a reagent cassette used for one measurement item, and the reagent cassette is provided with an information recording medium in which information regarding reagent suction positions of the reagent cassette is recorded. While the information recording medium is preferably attached to an upper surface of the reagent cassette from the viewpoint of simplifying an information read mechanism, it may be attached to any other suitable position, e.g., to a side or bottom surface of the reagent cassette. The information recording medium can be practiced by any one of various known media, such as a barcode label, a magnetic recording medium, and a contact/non-contact IC chip.

The information recorded in the information recording medium may further include the size and type of each reagent bottle placed on the reagent cassette, ID information of the reagent maker, the lot number of each reagent, and analysis parameters.

Moreover, plural reagent suction positions of the reagent cassette may be set in advance, and information regarding the presence or absence of the reagent bottle, the size of the reagent bottle, and the reagent type, such as a first or second reagent, may be stored for each of the reagent suction positions of the reagent cassette. For enabling the reagent bottles to be efficiently set in the analyzer, the reagent bottles can be formed in combination of suitable shapes, e.g., a sector and a rectangular parallelepiped.

The reagent cassette can be constructed, for example, such that each reagent bottle has a rectangular form with a horizontal cross-section of a certain size. When the reagent amount requires the size of the reagent bottle to be doubled, the size of the rectangular horizontal cross-section is doubled. Each rectangular space has an opening. When a plurality of reagent bottles are combined together, those reagent bottles can be arranged such that their openings lie on a linear line at certain intervals.

When reagents used for one measurement item cannot be placed in one reagent cassette, those reagents may be distributed to a plurality of reagent cassettes. In this case, the information required for each reagent cassette and each reagent bottle is attached per reagent cassette.

Information is set for each of the reagent cassettes. A plurality of positions where the reagent can be pipetted from the reagent cassette are given by the openings of the reagent bottles. The reagent cassette is provided with an information recording medium that stores information regarding the presence or absence of the opening of the reagent bottle for each of the reagent pipetting positions, and the size of each reagent bottle. In addition, a reagent identifier specifying reagent features, such as the reagent maker, the item code, and the cassette code, is written on a reagent identifier attached to the reagent cassette.

The reagent identifier used for the reagent cassette can be implemented as, e.g., a barcode label, an IC memory, or a magnetic tape. Any desired type of medium can be selectively used depending on the cassette shape, the cost of the reagent bottle, and the amount of information to be written in the medium.

After the reagent cassette has been registered, the automatic analyzer reads the information of the registered reagent cassette to determine the state of each reagent bottle (such as the size of the reagent bottle and whether the opening of the reagent bottle is present for each of the preset reagent suction positions). Since the reagent cassette stores the information of each reagent bottle, there is no need, in the automatic analyzer, of setting analysis conditions beforehand depending on the size of the reagent bottle, etc.

According to the present invention, the reagent cassette used in an automatic analyzer for a clinical examination room can be obtained which provides an analysis environment enabling an operator to select reagent bottles with proper capacities depending on the number of tests to be performed in each different type of facility and to properly set reagents with ease.

BRIEF DESCRIPTION OF THE DRAWINGS

FIG. 3 shows primary items of reagent cassette information;

FIG. 4 shows reagent information when one type of reagent is filled in a reagent bottle with a large capacity;

FIG. 5 shows reagent information when one type of reagent is filled in a reagent bottle with a small capacity;

FIG. 6 shows reagent information when two types of reagents are filled in a reagent cassette;

FIG. 7 illustrates an example of the case of filling a plurality of reagents used for the same measurement item in ore or more reagent cassettes;

DESCRIPTION OF THE PREFERRED EMBODIMENTS

Embodiments of the present invention will be described below with reference to the drawings.

First Embodiment

A first embodiment of the present invention will be described with reference to FIGS. 1 to 6.

Figure 1:
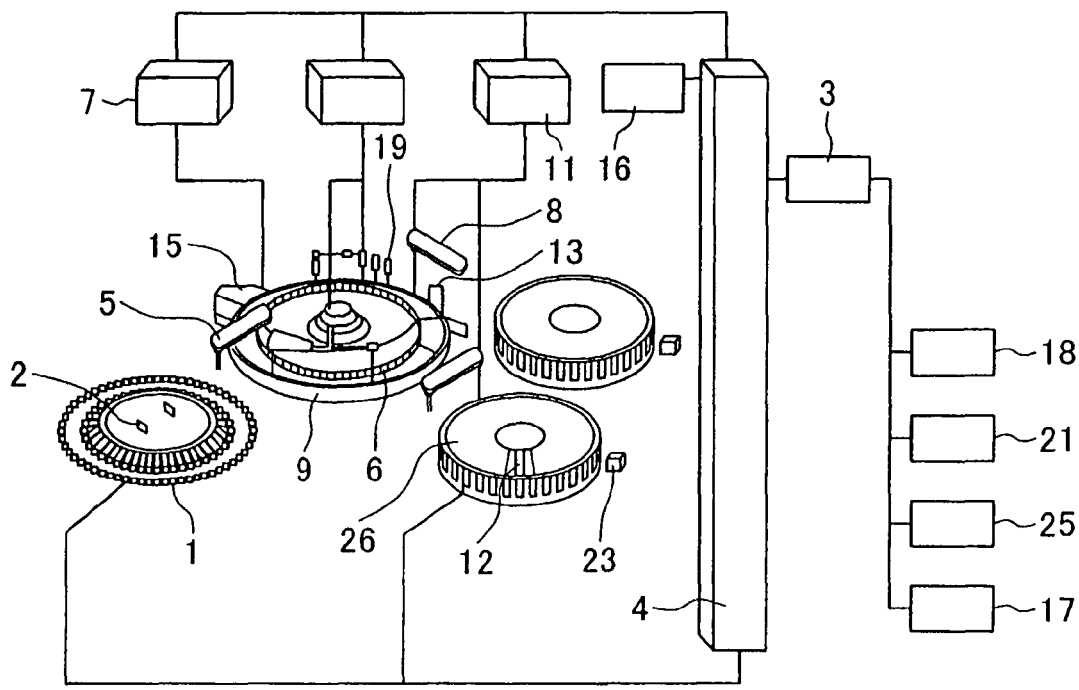
FIG. 1 is a block diagram of an automatic analyzer according to an embodiment of the present invention.

FIG. 1 is a block diagram of an automatic analyzer employing reagent cassettes according to an embodiment of the present invention.

Referring to FIG. 1, the automatic analyzer comprises a sample cup 1, a sample disk 2, a computer 3, an interface 4, a sample pipetting mechanism 5, a reaction cuvette 6, a sample pump 7, a reagent pipetting probe 8, a reaction tank 9, a reagent pump 11, a reagent cassette 12, a stirring mechanism 13, a multi-wavelength photometer 15, an A/D converter 16, a printer 17, a CRT screen 18 of a control panel, a washing mechanism 19, a keyboard 21, a reagent barcode reader 23, a hard disk 25, and a reagent disk 26. The hard disk 25 stores analysis parameters, the number of times of feasible analyses and the maximum number of times of feasible analyses for each reagent bottle, calibration results, analysis results, etc.

The analysis parameters include the item code assigned for each measurement item, the measurement wavelength, the amount of a sample to be pipetted, the calibration method, the concentration of a standard solution, the number of standard solution bottles, the check value in analysis abnormality, and the reagent cassette code required for each measurement item.

A reagent barcode attached to the reagent cassette 12 includes, as reagent information, the production lot number of each reagent, the size of each reagent bottle, the effective period of each reagent, and the sequence number of each reagent bottle. The sequence number is assigned as a different number per bottle so that individual reagent bottles can be recognized independently of each other.

The reagent cassette 12 is registered in the analyzer as follows. First, the reagent cassette 12 is set on the reagent disk 26 in an analysis section. Then, when a command for reading reagent information is entered, the reagent disk 26 starts rotation and the reagent barcode reader 23 reads the reagent barcode during the rotation of the reagent disk 26. The computer 3 searches for the relevant one from among the measurement items, for which the analysis parameters have already been registered, by using, as a key, the reagent cassette code included in the read information of the reagent barcode. Finally, the reagent information for each reagent cassette is stored in the hard disk 25.

The automatic analyzer is operated through steps of sampling, reagent pipetting, stirring, photometric measurement, washing of the reaction cuvette, and data processing, e.g., concentration conversion, in a successive manner as described in more detail below.

A plurality of sample cups 1 each containing a sample are placed on a rack. The rack is controlled by the computer 3 through the interface 4.

The rack is moved to a position just below the sample pipetting probe 5 in accordance with the order of samples to be analyzed. A predetermined amount of the sample in the relevant sample cup 1 is pipetted into the reaction cuvette 6 by the sample pump 7 coupled to the sample pipetting mechanism 5. The reaction cuvette 6 having received the pipetted sample is moved in the reaction tank 9 to a first-reagent adding position. A predetermined amount of first reagent is sucked from the reagent cassette 12 by the reagent pump 11 coupled to the reagent pipetting probe 8, and is added to the reaction cuvette 6 having been moved to the first-reagent adding position. After adding the first reagent, the reaction cuvette 6 is moved to a position of the stirring mechanism 13 where a first stage of stirring is performed. Those steps of addition and stirring are performed for the first to fourth reagents successively in a similar manner. The reaction cuvette 6 having been subjected to the steps of adding and stirring the reagents passes through a beam of light emitted from a light source, and the absorbance of the sample is detected by the multi-wavelength photometer 15. A detected absorbance signal is transmitted to the computer 3 through the A/D converter 16 and the interface 4, and is then converted into the concentration of the sample. Data converted into the concentration is outputted by a printer 17 through the interface 4. The reaction cuvette 6 having finished the photometric measurement is moved to a position of the washing mechanism 19. After the contents have been discharged, the reaction cuvette 6 is washed with water for use in the next cycle of analysis.

In the past, when preparing reagent bottles depending on the number of samples to be tested in each facility, an analyzer operator has been required to prepare plural sets of analysis parameters, the item codes, etc. in accordance with not only the size of each reagent bottle, but also the combination of reagent bottles, and to enter those analysis data in the computer beforehand.

Taking measurement of a blood glucose value (GLU) as an example, when two reagent bottles, i.e., one for 200 tests and the other for 400 tests, are prepared, separate item codes must be prepared because, if not so, a difficulty would arise in determining which one of the reagent bottles is to be used in the analysis. For that reason, in spite of one analysis item, plural sets of analysis parameters are required as given below.

Data Example in Analysis of GLU (Blood Glucose Value)

| Reagent Bottle Information | | |
|---|---|---|
| Reagent Bottle Type | 200 tests | 400 tests |
| Item Code | 01233 | 01234 |
| R1 Bottle Size | 100 ml; actually filled with 70 ml | 150 ml; actually filled with 140 ml |
| R2 Bottle Size | 20 ml; actually filled with 20 ml | 100 ml; actually filled with 40 ml |
| Analysis Parameters | | |

-continued

| | | |
|---|---|---|
| Number of Measurable Tests | 200 tests | 400 tests |
| Item Code | 01233 | 01234 |

In contrast, in the automatic analyzer according to the present invention, the analysis parameters depending on the size of each reagent bottle are recorded in the barcode serving as information recording medium, and the analyzer operator is no longer required to set the analysis parameters on the computer screen. Also, the reagent bottle can be formed in desired dimensions within the range until reaching the outer dimensions of the reagent cassette at maximum. While amounts of the first agent and the second agent consumed greatly differ depending on some of the analysis items, it is possible to select a proper one of plural reagent suction positions (bottle opening positions) and to increase flexibility in forming the reagent bottle (or the reagent cassette).

Figure 2:
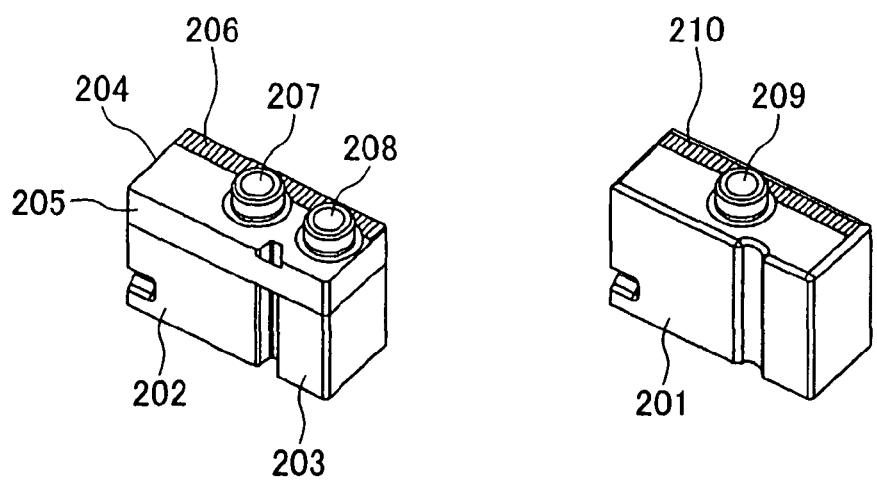
FIG. 2 illustrates an example of a reagent cassette including a combination of reagent bottles.

FIG. 2 illustrates an example of a reagent cassette according to the present invention and a combination of reagent bottles put together in the reagent cassette.

Referring to FIG. 2, a reagent cassette 204 comprises a reagent bottle 202 with a capacity of 70 ml, a reagent bottle 203 with a capacity of 35 ml, a bottle connector 205 for fixedly connecting the reagent bottle 202 and the reagent bottle 203 to each other, and a barcode label 206. Openings 207, 208 serve as reagent suction positions that are used when sucking reagents contained in the reagent bottles 202, 203, respectively. The barcode label 206 records thereon information regarding the size of each of the reagent bottles constituting the reagent cassette 204, the measurement item, and whether the opening of the reagent bottle is present for each of the preset reagent suction positions. Instead of recording whether the opening of the reagent bottle is present for each of the preset reagent suction positions, the information regarding the reagent suction position may be recorded in the form of coordinate values for positioning of the reagent pipetting mechanism (specifically the reagent pipetting probe).

As a result, the reagent pipetting mechanism is able to suck the reagent at the reagent suction position based on the information recorded on the barcode label.

In a practical example, a plurality of reagent bottles in each reagent cassette can be arranged side by side in the radial direction of the reagent disk 26, and information representing the reagent suction position as a position in the radial direction of the reagent disk 26 (i.e., in the lengthwise direction of the reagent cassette) can be recorded on the barcode label. The reagent suction position on the reagent disk (i.e., the position accessible by the reagent pipetting probe) is limited in many cases (though depending on a driving mechanism for the reagent pipetting probe). Stated another way, for example, when the reagent suction position is previously fixed in the circumferential direction of the reagent disk, the reagent suction position for the reagent cassette can be specified only with the information representing the reagent suction position as a position in the radial direction of the reagent disk 26 (i.e., in the lengthwise direction of the reagent cassette).

Returning to FIG. 2, a reagent bottle 201 with a capacity of 120 ml includes an opening 209 and a barcode label 210. Outer dimensions of the reagent bottle 201 are the same as those of the reagent bottle 204. Also, the position of the opening 209 is the same as that of the opening 207. While, in the illustrated embodiment, the barcode label 206 (210) is attached only to an upper surface of the reagent cassette (bottle), the position where the barcode label is attached and the number of attached barcode labels are optionally selectable.

When one type of reagent is used in a test for a certain analysis item, such as total protein (TP) or albumin (ALB), and the required amount of the reagent is small, one reagent bottle, i.e., the reagent bottle 202 or the reagent bottle 203, is set in the reagent cassette 204. When the required amount of the reagent is large, the reagent bottle 201 is employed.

When two types of reagents are used in a test for a certain analysis item, such as a blood glucose value (GLU), and the required amount of the reagent is small, the reagent cassette 204 is employed. More specifically, the first reagent is filled in the reagent bottle 202, and the second reagent is filled in the reagent bottle 203. These two reagent bottles 202, 203 are fixed together by using the regent connector 205. The manner of fixing the two reagent bottles together is not always limited to the use of the regent connector 205, and an adhesive tape may be instead used for fixing the two reagent bottles together.

FIG. 3 shows one example of reagent cassette information recorded on the barcode label according to the present invention.

The barcode label recording the information, shown in FIG. 3, thereon is attached to each reagent cassette.

FIG. 4 shows an example of reagent information recorded on the barcode label in accordance with the basic format of FIG. 3 when one type of reagent used in measuring the total protein (TP) is filled in the reagent bottle with a large capacity.

FIG. 5 shows an example of reagent information recorded on the barcode label in accordance with the basic format of FIG. 3 when one type of reagent used in measuring the total protein (TP) is filled in the reagent bottle with a small capacity.

FIG. 6 shows an example of reagent information recorded on the barcode label in accordance with the basic format of FIG. 3 when two types of reagents used in measuring the blood glucose value (GLU) are filled in the reagent cassette i.e., in the respective reagent bottles.

Second Embodiment

An automatic analyzer of this second embodiment has the same construction as that of the first embodiment. The automatic analyzer is used for clinical tests and comprises a sample pipetting section, a reagent pipetting section, a reaction cuvette, etc. To analyze one component in a sample by the automatic analyzer, a reagent bottle is constructed substantially in the form of a rectangular parallelepiped having a horizontal cross-section of a certain size corresponding to the measurement item using one or two types of reagents. When the reagent amount requires the size of the reagent bottle to be doubled, the reagent bottle is formed to have a horizontal cross-section with a doubled area. Each reagent bottle has an opening. When a plurality of reagent bottles are combined together, those reagent bottles are arranged such that their openings lie on a linear line at certain intervals.

The plurality of reagent bottles are combined together into a reagent cassette for each measurement item. In the reagent cassette, the positions of openings of the reagent bottles correspond to reagent cassette's positions where the reagents can be pipetted. Then, a reagent identifier is prepared which includes the reagent information regarding the presence/absence of the opening of the reagent bottle for each of the plural pipetting positions, the size of each reagent bottle, etc., and is attached to the reagent cassette.

Third Embodiment

An automatic analyzer of this third embodiment has the same construction as that of the first embodiment. The automatic analyzer is used for clinical tests and comprises a sample pipetting section, a reagent pipetting section, a reaction cuvette, etc. To analyze one component in a sample by the automatic analyzer, each measurement item employing one or two types of reagents is tested by using one reagent cassette in which a plurality of reagent bottles are combined together corresponding to the relevant measurement item, or by filling one type of reagent in one reagent cassette and combining two or more reagent cassettes together corresponding to the relevant measurement item. In this case, different reagent cassette codes are each set per reagent type for the same item code to determine the analysis parameters.

FIG. 7 illustrates examples of a reagent cassette according to the present invention and a combination of reagent bottles put together in the reagent cassette.

Referring to FIG. 7, the first reagent for measuring the blood glucose value is filled in a reagent bottle 202, and the second reagent for measuring the blood glucose value is filled in a reagent bottle 203. The reagent bottle 202 and the reagent bottle 203 are combined into one reagent cassette, and a barcode label 221 is attached to the reagent cassette. The barcode label 221 contains information regarding the opening positions of the reagent bottle 202 and the reagent bottle 203, the bottle sizes, the reagent types, and the cassette code. Alternatively, when larger reagent amounts are required, the first reagent for measuring the blood glucose value is filled in a reagent bottle 219 with a capacity of 300 ml, and the second reagent for measuring the blood glucose value is filled in a reagent bottle 201 with a capacity of 120 ml. A barcode label 223 contains information regarding the opening position of the reagent bottle 219, the bottle size, the reagent type, and the cassette code. A barcode label 222 contains information regarding the opening position of the reagent bottle 201, the bottle size, the reagent type, and the cassette code.

Figure 8:
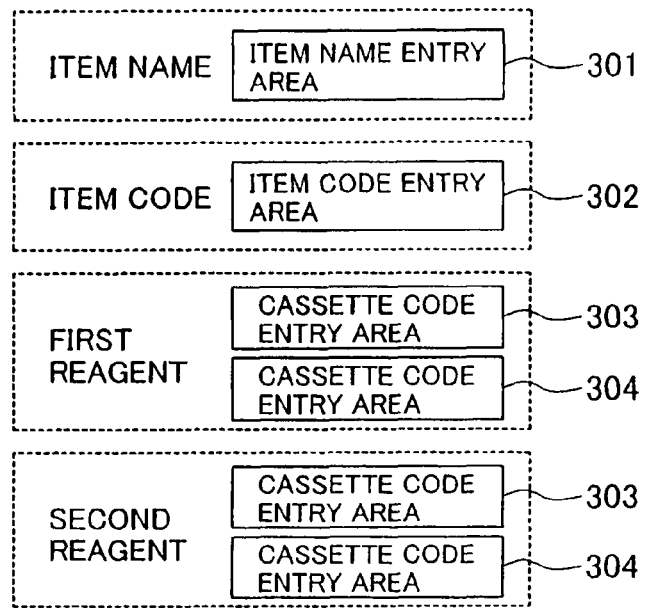
FIG. 8 illustrates an example of setting of analysis parameters in the case of filling a plurality of reagents used for the same measurement item in one or more reagent cassettes.
Figure 9:
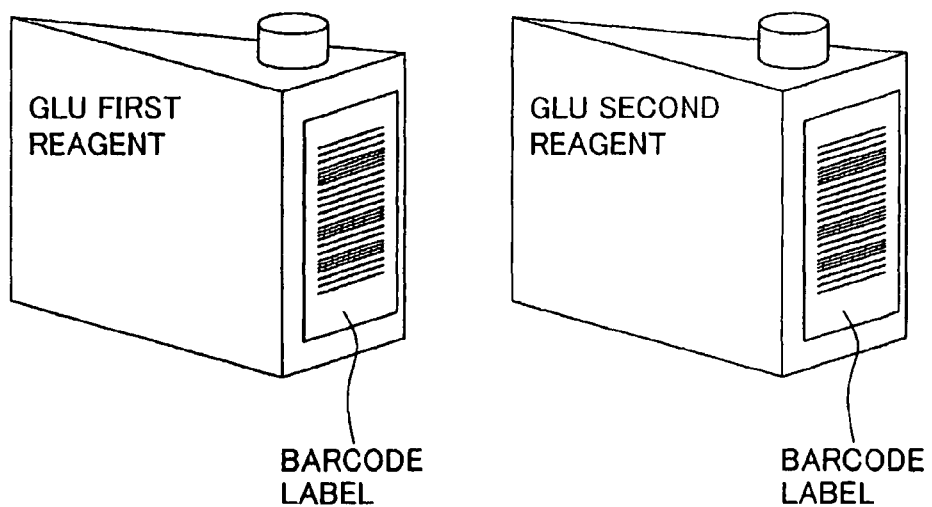
FIG. 9 is an illustration for explaining a known method of specifying information regarding the content of a reagent bottle for each reagent bottle.
Figure 10:
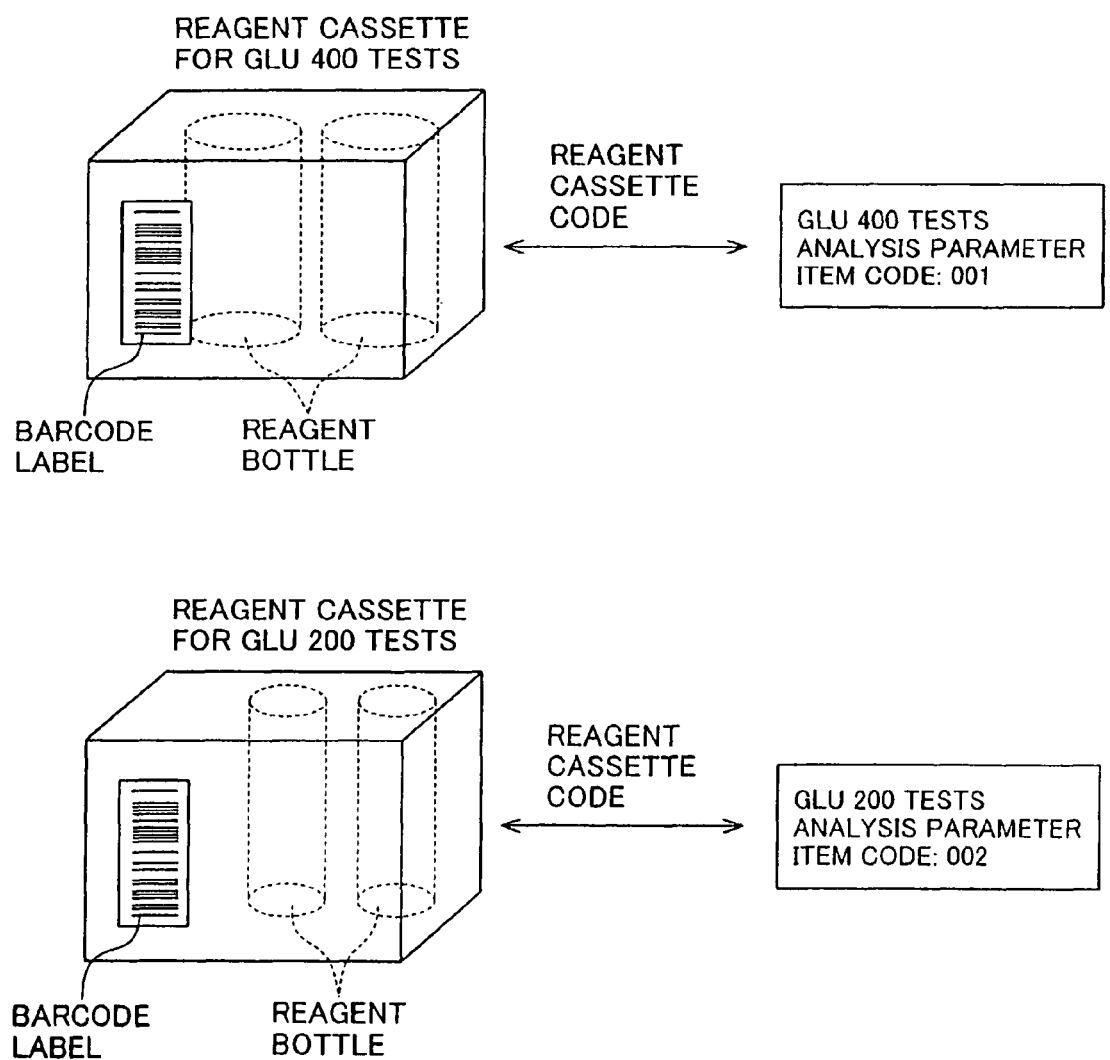
FIG. 10 is an illustration for explaining another known method of specifying information regarding all reagents on a reagent cassette.

FIG. 8 illustrates an example of an analysis parameter setting screen on which a plurality of reagent cassette codes can be each set per reagent type for the same measurement item. A description is made of, by way of example, the case of setting for measurement of the blood glucose value. As the name of the measurement item, "GLU" is entered in an item name entry area 301. As the item code assigned to the blood glucose value, "12345" is entered in an item code entry area 302. The cassette code of the first reagent for measuring the blood glucose value is entered in a cassette code entry area 303. When a plurality of reagent cassettes are used in a combined manner for the same measurement item as described above with reference to FIG. 7, another cassette code is entered in a cassette code entry area 304. For the second reagent for measuring the blood glucose value, the cassette code is likewise entered in at least one of a cassette code entry area 305 and a cassette code entry area 306.

What is claimed is:
1. An automatic analyzer comprising:
   a reagent disk;
   a plurality of reagent cassettes, each of which includes a plurality of reagent bottles used for one measurement item, being set on said reagent disk, each said reagent cassette being provided with a plurality of reagent sucking positions at predetermined locations on a top surface thereof;
   a reaction disk;
   a reaction cuvette arranged on said disk;

a reagent pipetting probe for sucking a reagent in said reagent bottles, and adding a reagent into a sample in said reaction cuvette;

a photometer for detecting an absorbance of said sample;

an information reading mechanism; and a control mechanism for controlling a reagent pipetting position at said reagent disk, controlling said reagent pipetting probe to move to said reagent pipetting position to suck a reagent from said reagent bottle in said reagent cassette positioned at said reagent pipetting position and to add a sucked reagent into said reaction cuvette on said reaction disk, and converting said absorbance of said sample into a concentration of said sample, wherein each said reagent cassette is provided with a single information recording medium on a top surface of said cassette in which information regarding at least reagent suction positions of said reagent cassette, the presence or absence of a reagent bottle at each reagent sucking position and a size of each reagent bottle, is recorded, and said information reading mechanism is adapted to read the information recorded in the information recording medium provided on each said reagent cassette, and said control mechanism controls the reagent pipetting position in accordance with the information regarding each of the reagent suction positions read by said information reading mechanism and controls the amount of reagent sucked from each reagent bottle in accordance with the information regarding the size of each reagent bottle read by said information reading mechanism.

2. The automatic analyzer according to claim 1, wherein said reagent bottles are fixedly connected to each other by using a bottle connector.

3. The automatic analyzer according to claim 1, wherein said reagent cassette is substantially in the form of a rectangular parallelepiped, and said information recording medium records said reagent suction positions in the lengthwise direction of said reagent cassette.

4. The automatic analyzer according to claim 1, wherein said information recording medium further records ID information of a reagent maker and information regarding a reagent lot.

5. The automatic analyzer according to claim 1, wherein said information recording medium further records information regarding analysis parameters.

6. The automatic analyzer according to claim 1, wherein said reagent cassette has a constant horizontal cross-sectional area, and when a reagent amount is required in excess of a capacity of said reagent cassette, a plurality of reagent cassettes are joined to each other such that respective openings of said reagent cassettes lie on a linear line.

* * * * *